United States Patent
Lange

(10) Patent No.: US 8,457,748 B2
(45) Date of Patent: Jun. 4, 2013

(54) VAGUS NERVE STIMULATION FOR THE TREATMENT OF FIBROMYALGIA

(75) Inventor: Gudrun Lange, Lake Hopatcong, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 583 days.

(21) Appl. No.: 12/322,741

(22) Filed: Feb. 6, 2009

(65) Prior Publication Data

US 2009/0264959 A1    Oct. 22, 2009

Related U.S. Application Data

(60) Provisional application No. 61/065,987, filed on Feb. 14, 2008.

(51) Int. Cl.
*A61N 1/00*    (2006.01)

(52) U.S. Cl.
USPC .................. 607/46; 607/2; 607/115

(58) Field of Classification Search
USPC ................................. 607/2, 46, 115
See application file for complete search history.

(56) References Cited

U.S. PATENT DOCUMENTS 5,514,175 A * 5/1996 Kim et al. ............ 607/136
6,168,569 B1 * 1/2001 McEwen et al. ........... 600/557

* cited by examiner

*Primary Examiner* — Nicole F Lavert
(74) *Attorney, Agent, or Firm* — Licata & Tyrrell P.C.

(57) ABSTRACT

This invention relates to the use of vagus nerve stimulation for the treatment of fibromyalgia which comprises applying a therapeutic stimulation signal from a stimulus generator, when activated, to at least some of plural electrodes implanted in stimulating relation of the patient's vagus nerve and activating the stimulus generator to generate the therapeutic stimulation signal to alleviate the pain under treatment.

3 Claims, No Drawings

VAGUS NERVE STIMULATION FOR THE TREATMENT OF FIBROMYALGIA

This application claims priority of U.S. Provisional Application Ser. No. 61/065,987, filed Feb. 14, 2008.

This invention was made in part with government support under grant number R01 AR53732 awarded by NIAMS. The government has certain rights in the invention.

This invention relates to the use of vagus nerve stimulation for the treatment of fibromyalgia.

BACKGROUND OF THE INVENTION

Fibromyalgia Syndrome (FMS) is a chronic pain disorder of unknown origin, characterized by diffuse body pain and tenderness. Evidence is accumulating that the pathogenesis of FMS may be associated with central dysregulation of pain regulatory systems manifesting itself psychophysically in abnormally high pain sensitivity and intolerance thresholds. Conventional drug and behavioral therapies have proven to be largely unsuccessful in relieving FMS pain over time. While opioid maintenance therapy, the current 'last resort' treatment option for FMS patients with severe, unrelenting pain, is efficacious, it is often avoided for fear of addiction. Thus, unrelieved FMS pain leads to poor quality of life, disability, economic disadvantage, and overutilization of the health care system. At this point in time, a cure for FMS does not exist. It has been estimated that less than half of all FMS patients experience adequate pain relief with conventional behavioral and pharmacological therapies. Thus an effective treatment for FMS is not yet available.

Based on physiological data derived from animals and psychophysical data derived from humans, VNS was found to reduce the intensity of laboratory pain, especially when sensitization of the central pain regulatory system, known as wind-up, was induced thought to underlie the chronic pain associated with FMS.

Fibromyalgia Syndrome (FMS) is a chronic disorder characterized by widespread musculoskeletal pain often accompanied by other symptoms including fatigue and depression. The diagnosis of FMS is made according to guidelines of the American College of Rheumatology and can be made if a patient has suffered from widespread pain lasting for at least three months and is present in all four quadrants of the body. Additionally, patients must report pain on 4 kg pressure at 11 or more of 18 established tender points. The ACR criteria do not differentiate between primary FMS or FMS secondary to rheumatic disorders, and thus, FMS is not a diagnosis of exclusion. FMS occurs most commonly in women between the ages of 20 and 50 years. The illness is common, seen in 3.4% of women, and 0.5% of men. Thus, FMS is a significant public health concern.

The etiology of FMS is still unknown, and no consistent underlying mechanism has been identified. However, evidence is accumulating that the pain regulatory system in FMS patients may be centrally disturbed. This dysregulation hypothesis is primarily based on experimentally induced pain studies showing that FMS subjects have lower pressure, heat, and cold pain thresholds and lower pressure pain tolerances at both tender and non-tender sites than controls. In addition, exercise and diffuse noxious inhibitory control (DNIC) manipulations, which are known to result in increased pain thresholds in healthy control subjects, have not had the same effect on pain thresholds in patients with FMS. Further support for the dysregulation hypothesis comes from biochemical studies examining spinal cord indices of pain transmission such as substance P and the biogenic amines. FMS patients have been shown to exhibit significantly elevated substance P levels and low cerebral spinal fluid levels of 5-hydroxyindole acetic acid (5-HIAA), 3-methoxy-4-hydroxyphenethylene glycol (MHPG), and homovanillic acid (HVA); the metabolites of serotonin, norepinephrine, and dopamine, respectively. These biochemicals have well-established roles in pain processing and abnormal spinal cord levels suggest that there may be an increase in nociceptive transmission combined with a decrease in the centrally regulated descending inhibition of the nociceptive signal in people with FMS.

A management protocol for the conventional treatment of FMS pain has been recently proposed and was adopted to characterize patients to be included in this study. Generally the first level of treatment includes nonsteroidal anti-inflammatory drugs (NIAISDs), often used in combination with tricyclic antidepressants (TCAs). However, efficacy of NSAIDS, (including aspirin) in treating FMS pain is limited and TCAs, although some analgesic effects have been found at low doses, only achieve clinically significant pain reduction in 25% to 30% of FMS patients. If sufficient pain relief is not achieved at level 1, the treatment moves up to level 2-substitution with or addition of anti-epileptic drugs (AEDs). Failure to achieve pain relief at level 2, then gives rise to trials at the next, third level, with alpha(2) adrenergic agonists (i.e. Tizanidine) and non-opioid analgesics (e.g., lidocaine patches). The treatment option of 'last resort' is use of short or long-acting opioid analgesics, a few of which (i.e. Tramadol, MS-Contin) have moderate efficacy in treating severe FMS pain. However, physicians and patients often eschew this treatment choice for fear of legal or medical complications, including opiate abuse and addiction. Of all the agents used to manage FMS pain, the class of Selective Serotonin Reuptake Inhibitors (SSRIs) is the least efficacious of all. Also, it has to be kept in mind, that all pharmacological treatment options have side effects (e.g., nausea, weight gain, dizziness), making it often difficult for FMS patients to tolerate many medications prescribed to them for pain relief. Thus, FMS patients are often left under treated either because of lack of efficacy or due to intolerable side effects often resulting in impaired quality of life, disability, economic disadvantage, and increased health care utilization.

The bleak treatment outlook for patients with FMS is highlighted by a prospective, longitudinal study conducted in 6 tertiary care rheumatology centers in the US. Researchers examined health care utilization, health status and disease severity in 538 FMS patients with median duration of disease of 7.8 years. Over the time of the study, participants used an average of 8 different drugs separately or in combination. NSAIDs were used by 90.9% of the study participants for an average duration of 5.6 months. The second most commonly prescribed class of drugs was TCAs (57.3%). At the conclusion of Wolfe's 7-year study, FMS patients had visited a "traditional" health care provider on average 10 times per year, a "non-traditional" provider 12 times per year, and had been hospitalized once every 3 years for FMS-associated symptoms. 94-98% of the patients continued to experience pain at the conclusion of the study. In fact, the mean severity of pain (1.6 on a 0-3 Visual Analog Scale; VAS) did not change over the course of the study. Importantly, despite no change in pain scores, work disability increased significantly over time. These data suggest that inadequate FMS pain management over time is associated with increased work disability. This conclusion is supported by findings of a more recent study in a community sample of 100 FMS patients. 87% of patients reported that they "had to reduce their work or school hours since the onset of their pain," 31% reported work disability, and 47.5% experienced reductions in income since the onset of FMS associated pain. Importantly, White et al. found that one of the leading clinical predictors for an increased risk of work disability was pain severity of ≧75 mm on a 100-mm visual analog scale (VAS). We interpret these data to mean that work disability is a marker for the degree of refractoriness or severity that is indicative of insufficient pain management.

Very commonly the lives of patients with severe, unrelieved FMS pain are further complicated by concurrent major depression. Prevalence of lifetime depressive disorder in FMS is higher than in the general population. Approximately 80% of FMS patients seeking tertiary care have a concurrent diagnosis of depressive disorder. Depression in the face of FMS significantly increases the risk for poor physical functioning and poor quality of life. Epstein and colleagues assessed quality of life in FMS patients, in the general population, and in patients suffering from other chronic disorders, such as depression alone, heart disease, and arthritis. Every SF-36 subscale score was lowest in FMS! Taken together, these data suggest that patients with unrelieved FMS pain who are disabled and suffer from concurrent depression comprise the most refractory, severely ill segment of patients with FMS.

Thus, an object of this invention is to provide additional effective therapy for FMS patients. More particularly, it is an object of the invention to provide therapy to reduce pain associated with fibromyalgia. An additional object of the invention is to provide sufficient therapy to a patient suffering from fibromyalgia to allow the patient to return to work.

SUMMARY OF THE INVENTION

It has now been found that vagus nerve stimulation (VNS) can be a viable adjunctive treatment option for FMS patients. It has been found that VNS treatment can not only reduce tender point threshold, in some cases the threshold was reduced to the degree that the point tested was actually no longer tender. Thus, VNS has the potential to be a breakthrough non-pharmacological treatment modality to relieve FMS pain.

More particularly, fourteen (14) patients were enrolled in a single-center study using VNS in a group of FM patients refractory to conventional pharmacological treatment. To be eligible for enrollment into the study, FM patients had to provide physician documented evidence that they had tried NSAIDS, tricyclic antidepressants or duloxetine, at least one anti-epileptic drug, and tramadol to relieve FM pain but without sufficient relief or with poor tolerance. Potential participants were allowed to remain on these medications, but they did not have to be on them to participate. Patients had to be on a stable medication regimen for at least 4 weeks prior to study entry and could not increase or change this regimen throughout the acute phase of the study.

The diagnosis of FMS requires 4 quadrant plus axial pain as well as at least 11 of 18 tender points. By the end of the acute study phase after 3.5 months of VNS, 4 of the 12 patients fulfilled neither of these criteria, one additional patient no longer fulfilled the tender point criterion and another the widespread pain criterion. Eleven patients were followed out to 6 months: 7 no longer fulfilled formal criteria for FMS at that timepoint. Seven of the 11 patients in follow up have completed the 9 months study visit—none of them carries the diagnosis of FMS anymore.

The criteria used to determine a minimally clinically important difference (MCID) for post-implantation study visits required patients to show improvement on three separate measures: a 30% improvement on median pain scores via the electronic diary AND a patient global assessment of change score of +1 (very much improved) to +3 (minimally improved) on a 7 point scale going through 0 (no change) to +7 (very much worse) AND an improvement of at least 6 points on the Physical Composite Score of the SF-36, a commonly used questionnaire for health-related quality of life. At the end of the acute study phase, usable data on 12 patients was obtained; five of these fulfilled all three criteria for improvement and 9 for the first two criteria only.

The results are shown in Table 1 which shows primary outcome measures for the acute study (visit 12) and the last available subsequent visit (PGIC, patient global impression of change; Usual Pain Severity, rating of usual pain since last visit). Results indicated by (1) are positive, (2) are equivocal and (3) are negative.

TABLE 1

| ID | Last Visit | Visit | PGIC* 12 | Last | Usual Pain Severity** 2 | 12 | Last | SF-36 Physical Composite Score*** 2 | 12 | Last |
|---|---|---|---|---|---|---|---|---|---|---|
| 3 | 15 | | 2(1) | 1(1) | 10 | 5(1) | 3(1) | 29.5 | 34.6(1) | 48.4(1) |
| 1 | 15 | | 3(1 | 3(1) | NA | 2 | 4 | 27.9 | 31.4(1) | 31.2(1) |
| 2 | 15 | | 2(1) | 2(1) | 9 | 5(2) | 5(2) | 23.7 | 35.6(1) | 36.0(1) |
| 4 | 15 | | 4(3) | 4(3) | 9 | 6(2) | 7(3) | 31.4 | 42.8(1) | 38.5(1) |
| 5 | 15 | | 1(1) | 1(1) | 9 | 0(1) | 2(1) | 26.7 | 41.8(1) | 38.0(1) |
| 6 | 15 | | 1(1) | 1(1) | 7 | 4(1) | 0(1) | 19.4 | 50.8(1) | 49.0(1) |
| 7 | 14 | | 1(1) | 1(1) | 10 | 6(2) | 5 | 23.5 | 21.(3) | 44.0(1) |
| 8 | 13 | | 1(1) | 2(1) | 8 | 1(1) | 1(1) | 22.6 | 45.0(1) | 39.1(1) |
| 9 | 13 | | 2(1) | 1(1) | 8 | 4(1) | 2(1) | 31.4 | 42.4(1) | 47.5(1) |
| 13 | 12 | | 2(1) | 2(1) | 8 | 5(2) | 5(2) | 36.2 | 30.3(3) | 30.3(3) |
| 11 | 13 | | 1(1) | 2(1) | 9 | 6(2) | 8(3) | 31.0 | 18.6(3) | 34.7(2) |
| 10 | 13 | | 1(1) | 1(1) | 7 | 6(2) | 5(2) | 21.1 | 41.5(1) | 42.6(1) |
| Mean | | | 1.7 | 1.7 | 8.5 | 4.2 | 3.9 | 27.0 | 36.4 | 39.9 |
| Std. Dev. | | | 0.97 | 1.0 | 1.0 | 2.08 | 2.39 | 5.06 | 9.59 | 6.42 |

*1 = Markedly Improved; 2 = Moderately Improved; 3 = Mildly Improved; 4 = Same
**0-10 rating scale
***in units of T-scores relative to a national normative sample (Mean = 50, SD = 10)

By the end of the acute study phase, ten of the 12 patients reported they had reduced medications with two stopping methadone and oxycontin respectively, 3 reducing doses of acetaminophen/hydrocodone, 1 stopping tramadol, 3 reducing its dose and 1 reducing trazadone.

DETAILED DESCRIPTION OF THE INVENTION

The notion that VNS could be a viable adjunctive treatment option for patients with refractory FMS is based on the encouraging results of pre-clinical and clinical research studies suggesting that VNS THERAPY may target CNS processes involved in pain transmission at both spinal and supraspinal levels and could thus have a beneficial effect on pain associated with FMS.

VNS THERAPY is generally well tolerated by most patients with epilepsy and depression and is rarely the cause for VNS discontinuation and explanation. Reported side effects are either associated with surgery and/or stimulation on-periods. The most common surgery-related events are infections. The most common side effects during actual stimulation can include voice alteration, hoarseness, cough, paresthesia, headache, throat pain, nausea, and dyspnea. In fact, in studies of VNS for epilepsy the following side effects listed were the only ones occurring in more than 5% of the study participants only during actual stimulation (intermittently), improved over time, and could be alleviated or minimized by changing the stimulation parameters: voice alteration (50%), increased coughing (41%), numbness/tingling (28%), sore throat (27%), nausea (19%), shortness of breath (18%) and indigestion (12%)[21]. The manufacturer of the device, Cyberonics, Inc., followed 253 refractory epilepsy patients up to 3 years after implantation. All patients received stimulation according to a standard epilepsy VNS stimulation protocol. All of the reported stimulation-related side effects diminished over time; only 7.8% and 4.5% of patient's still reported hoarseness and headache, respectively, after two years. After three years, shortness of breath was the most common stimulation related side effect, reported by 3.8% of the 253 patients followed. Severe adverse events were limited to respiratory difficulties (n=3) and severe hoarseness (n=3). Median seizure decreases of 31.1%, 40.7%, and 40.4% were reported for one, two, and three-year follow-ups, respectively. Thus, even though mild to moderate side effects may occur due to stimulation, the benefits of the treatment over time were considerable. The safety profile for patients with treatment resistant depression is similar to that seen in epilepsy. VNS has been approved in the US for clinical use in treatment resistant epilepsy and in Canada and Europe also for treatment-resistant depression. At its most recent meeting on Jun. 15, 2004, the FDA's Center for Devices and Radiological Health Advisory Committee, recommended VNS THERAPY for approval as an adjunctive treatment for depression in the US.

VNS THERAPY System is manufactured by Cyberonics, Inc., Houston, Tex. The System consists of the implantable, multi-programmable VNS THERAPY Model 102 bipolar pulse generator, the Model 302 VNS THERAPY bipolar leads, and the external programming system used to set and change stimulation settings as well as to perform system diagnostics. The pulse generator is housed in a hermetically sealed titanium case and will deliver electrical signals to the vagus nerve powered by a single battery. Electrical signals are transmitted from the pulse generator to the vagus nerve via the bipolar lead. The external programming system includes the Model 201 Programming Wand, the Model 250 Software, and a compatible laptop computer. Together these three components provide communication with the pulse generator, so called telemetry. Telemetry allows for non-invasive programming, functional assessments (device diagnostics), device interrogation, and data retrieval. A system of multiple checks verifies the integrity of communications; each parameter is programmed and verified individually. Magnets for patient use are also provided as part of the VNS THERAPY System. They can either be worn on the patient's watchband (watch-style) or belt (pager-style) and can be placed over the pulse generator to activate stimulation or to inhibit stimulation. Normal programmed stimulation resumes when the magnet is removed. All patients will be trained in the use of the magnet and will practice the use of the magnet as part of their first programming visit.

The implantable VNS THERAPY System has been reliable and safe when used in accordance with its labeling. Nerve histology collected from two patients stimulated for more than one year indicates that no significant nerve damage occurs over time from normal vagus nerve stimulation. A wide range of animal studies indicates that stimulation at a frequency <50 Hz at duty cycles of less than 50% should not cause nerve damage. Additionally, continuous stimulation at lower frequencies (10 to 20 Hz) should not cause nerve damage and did not cause nerve damage in two patients treated in an epilepsy clinical study who inadvertently received continuous stimulation for two weeks (PMAA, 1994). Excessive stimulation at a combination of high frequency (2 Hz) and an excess duty cycle (greater than 50%) has resulted in degenerative nerve damage in laboratory animals.

EXAMPLES

Aim of Investigation

Fibromyalgia (FM) is a potentially disabling chronic pain disorder characterized by 4-quadrant plus axial pain of at least 3 months duration and at least 11 of 18 tender points. Vagus Nerve Stimulation (VNS) has been shown to be safe, tolerable, and efficacious for patients with treatment-resistant epilepsy and depression. In both patient groups, stimulation of the left vagus nerve has been reported to reduce pain perception. A Phase I trial to evaluate the tolerability, safety and efficacy of VNS implantation and stimulation in patients with FMS refractory to conventional pharmacological treatment was carried out.

Patients were 21 to 55 years of age with at least average overall intellectual function and all were physician-diagnosed with FMS for at least 2 years. In order to qualify for entry, potential study participants had to report widespread pain—i.e., median scores of at least 5—on a watch-type electronic diary (Minimitter) that polled them about their pain five times a day on a 0 to 10 severity scale over 9 days. Individuals were excluded from participation if they were in litigation at time of enrollment, reported the onset of FM following physical trauma, or had psychotic depression, bipolar disorder, psychotic disorders, or substance abuse/dependence within 10 years as determined by psychiatric diagnostic interview. Additional exclusion factors included use of antipsychotic drugs within 3 months of enrollment, use of any non-pharmacological treatment for FMS within 2 months of enrollment, history of heart disease, a pulmonary condition resulting in an ASA score of greater than III, or a unilateral or bilateral vagotomy.

Study Procedures

Subsequent to recruitment into the study, participants signed a screening consent to allow the study team to gather additional information for final study inclusion for implantation. The diagnosis of FMS was confirmed on two Center visits by history (patient reported having pain in all 4 bodily quadrants plus having axial pain in chest or neck—denoted as 4+A in Table 1) and physical examination (palpation at each of the 18 tender points with 4 kg of force producing tenderness of 3 or greater on a 0 to 10 Likert pain scale where 0 was no pain, 5 moderate pain and 10 worst pain possible). Once all information was obtained under the screening protocol, FMS patients signed an enrollment consent. On average about 3 months after signing the enrollment consent, study participants were implanted with the VNS device. Most of this time period was utilized for pre-op testing, scheduling surgery, and other activities related to the startup of the individual trial. During the baseline period, the study participant came to the study center for 2 scheduled visits to obtain baseline measures. Implantation of the device was followed by a 2-week post-surgery recovery period, a 2-week ramp-up/stimulation adjustment period, and a 12 week period of fixed stimulation treatment, referred to as "Acute Study." After completion of the acute study, participants were able to elect to be enrolled in the follow up study with study visits at 6, 9, and 12 months post implantation.

Patients were assessed approximately every 2 weeks after surgery until the end of the acute study phase 4 months later to assess safety, patient tolerance of VNS and to do psychophysical heat pain testing where participants were randomly presented 7 stimuli ranging from 43° C. to 49° C. in one-degree increments on 2 random trials for a total of 14 stimulus presentations. In addition, patients wore a watch-type electronic diary for a period of 9 days before surgery and before the end of the acute study phase; the device queried them about their immediate pain level on a 0 to 10 Likert scale five times a day.

Methods

The treatment study of fibromyalgia used the Model 102 VNS THERAPY System (Cyberonics, Inc., Houston, Tex.). Following surgical implantation of the device into eligible participants and a 2-week recovery period, stimulation (30 sec on, 5 min off Duty Cycle, 20 HZ, PW=250 μsec) was increased to as much as 2 mA over a 2-week adjustment period and maintained during a 12-week acute study period. The primary efficacy endpoints evaluated global impression of change and changes in ratings of pain intensity and ratings of physical function (SF-36). Adverse events related to implantation and stimulation were recorded.

Results

Primary Preliminary Efficacy Outcome.

Table 2 provides a summary of the FMS status of each participant on baseline and on each of the follow up evaluations. The diagnosis of FMS requires 4 quadrant plus axial pain as well as at least 11 of 18 tender points. By the end of the acute study phase after 3.5 months of VNS, 4 of the 12 patients fulfilled neither of these criteria, one no longer fulfilled the tender point criterion and one the widespread pain criterion. Ten patients were followed out to 6 months: 5 no longer fulfilled both criteria and 3 no longer fulfilled the tender point criterion—leaving just 3 of 10 with formal criteria for FMS.

TABLE 2

Number of Tender Points and (Painful Quadrants) Over Time

| Participant | Baseline (Avg) | Acute Study Phase End | 6 months | 9 months | 12 months |
|---|---|---|---|---|---|
| 1 | 12 (4 + A) | 5 (4 + A) | 3 (4) | 7 (4 + A) | 8 (4 + A) |
| 2 | 18 (4 + A) | 11 (4 + A) | 5 (0) | 1 (0) | 4 (0) |
| 3 | 15.5 (4 + A) | 12 (4 + A) | 8 (4 + A) | 6 (2 + A) | 3 (3) |
| 4 | 12.5 (4 + A) | 4 (3 + A) | 5 (2 + A) | STOP | EXPLANT |
| 5 | 18 (4 + A) | 0 (4) | 1 (4 + A) | 1 (0 + A) | 3 (2) |
| 6 | 16 (4 + A) | 4 (1) | 4 (2 + A) | 7 (0) | 6 (2) |
| 7 | 18 (4 + A) | 12 (4 + A) | 16 (4 + A) | 6 (3 + A) | ND |
| 8 | 15 (4 + A) | 0 (1) | 7 (4 + A) | 8 (4 + A) | ND |
| 9 | 18 (4 + A) | 18 (4 + A) | 5 (0) | 1 (1 + A) | ND |
| 10 | 18 (4 + A) | 18 (4) | 18 (4 + A) | ND | ND |
| 11 | 18 (4 + A) | 18 (4 + A) | 18 (4 + A) | ND | ND |
| 12 | 13.5 (4 + A) | | DROPPED FROM STUDY | | |
| 13 | 12.5 (4 + A) | 13 (3 + A) | ND | | |
| 14 | 18 (4 + A) | | DEVICE PROBLEM | | |

ND = Not Determined

CONCLUSIONS

Efforts to date have not suggested unusual safety or tolerability issues when implanting a VNS system in patients with FM. This result, coupled with assessments of efficacy that are consistent with beneficial effects on pain intensity and physical function, encourage larger-scale evaluations of VNS in the treatment of FM.

Although a best mode of practicing the invention has been described herein with reference to certain preferred embodiments and methods of treating FMS, it will be understood by those skilled in the field from a consideration of the foregoing disclosure, that variations and modifications of the described embodiments and methods may be made without departing from the spirit and scope of the invention. Accordingly, it is intended that the invention shall be limited only to the extent required by the appended claims and the rules and principles of applicable law.

The invention claimed is:

1. A method of reducing the severity of symptoms in patients suffering from fibromyalgia syndrome (FMS) comprising:

a) determining a baseline level of pain in a patient;
b) surgically implanting electrodes in the patient connected directly to a patient's vagus nerve so that the patient's vagus nerve can be selectively and directly stimulated;
c) applying a therapeutic stimulation signal from a stimulus generator to the electrodes and stimulating the vagus nerve, wherein said therapeutic stimulation signal is up to 2 mA and is applied continuously for at least 12 weeks; and
d) determining a level of pain in the patient following application of therapeutic stimulation in step c), wherein a decrease in the level of pain following application of therapeutic stimulation in step c) as compared with the baseline level of pain is indicative of a reduction in the severity of FMS symptoms.

2. The method of claim 1, wherein the therapeutic stimulation signal is an electrical pulse signal.

3. The method of claim 1, wherein the stimulus generator is adapted for manual activation by the patient.

* * * * *